United States Patent [19]

O'Hara et al.

[11] Patent Number: 4,565,898

[45] Date of Patent: Jan. 21, 1986

[54] DEHYDROGENATION OF DEHYDROGENATABLE HYDROCARBONS

[75] Inventors: Mark J. O'Hara; Tamotsu Imai, both of Mount Prospect; Jeffery C. Bricker, Des Plaines; David E. Mackowiak, Mount Prospect, all of Ill.

[73] Assignee: UOP Inc., Des Plaines, Ill.

[21] Appl. No.: 708,832

[22] Filed: Mar. 6, 1985

[51] Int. Cl.$^4$ .............................................. C07C 5/333
[52] U.S. Cl. .................................... 585/441; 585/319; 585/330; 585/444; 585/445; 585/660; 585/661
[58] Field of Search ............... 585/319, 330, 440, 441, 585/444, 445, 660, 661

[56] References Cited

U.S. PATENT DOCUMENTS

| | | | |
|---|---|---|---|
| 3,437,703 | 4/1969 | Reitmeier et al. | 260/669 |
| 3,670,044 | 6/1972 | Drehman et al. | 585/658 |
| 3,855,330 | 12/1974 | Mendelsohn et al. | 585/441 |
| 3,904,703 | 9/1975 | Lo et al. | 585/661 |
| 4,435,607 | 3/1984 | Imai | 585/443 |

*Primary Examiner*—John Doll
*Assistant Examiner*—A. Pal
*Attorney, Agent, or Firm*—Thomas K. McBride; William H. Page, II; Raymond H. Nelson

[57] ABSTRACT

Dehydrogenatable hydrocarbons may be subjected to a dehydrogenation reaction in which the hydrocarbons are treated with a dehydrogenation catalyst comprising a modified iron compound in the presence of steam in a multicatalyst bed system. The reaction mixture containing unconverted hydrocarbons, dehydrogenated hydrocarbons, hydrogen and steam is then contacted with an oxidation catalyst whereby hydrogen is selectively oxidized in preference to carbon dioxide and carbon monoxide or hydrocarbons. The selective oxidation of hydrogen will improve the combustion thereof and supply the necessary heat which is required for a subsequent dehydrogenation treatment. The selective oxidation catalyst which is used will comprise a noble metal of Group VIII of the Periodic Table and, if so desired, a metal of Group IA or IIA of the Periodic Table composited on a porous inorganic support. The inorganic support will have been calcined prior to impregnation thereof at a temperature in the range of from about 900° to about 1500° C. in the absense or presence of steam to provide a catalyst which possesses increased stability and activity when compared to prior catalysts.

20 Claims, No Drawings

DEHYDROGENATION OF DEHYDROGENATABLE HYDROCARBONS

BACKGROUND OF THE INVENTION

It has been known in the prior art that unsaturated hydrocarbons may be obtained from the dehydrogenation of dehydrogenatable hydrocarbons. The dehydrogenation may be effected by subjecting the dehydrogenatable hydrocarbons to a dehydrogenation process at dehydrogenation conditions in the presence of certain catalytic compositions of matter which possess the ability to dehydrogenate said compounds with the resultant formation of olefinic hydrocarbons. The particular dehydrogenation catalysts which are employed are well known in the art and comprise such compounds as nickel composited on a solid support such as diatomaceous earth, kieselguhr, charcoal and iron composited on the same supports, etc.

Other dehydrogenation processes have employed, in addition to the dehydrogenation catalysts, an oxidation catalyst in the reaction process. The presence of the oxidation catalyst is necessitated by the fact that it is advantageous to oxidize the hydrogen which is produced by contact with an oxygen-containing gas in order to maintain the desired reaction temperature. For example, styrene, which is an important chemical compound utilized for the preparation of polystyrene, plastics, resins or synthetic elastomers such as styrene-butadiene rubber, etc., may be prepared from the dehydrogenation of ethylbenzene. The dehydrogenation of ethylbenzene into styrene, which is effected by treating ethylbenzene with steam in the presence of a modified iron catalyst, is endothermic in nature. The heat of reaction is about 30 Kcal per mole of ethylbenzene. Therefore, the temperature of the catalyst bed decreases significantly during the progress of the reaction in a commercial adiabatic reactor resulting in limitation of ethylbenzene conversion to a low level. The limitation of conversion arises from the fact that the equilibrium conversion of ethylbenzene is lowered and the rate of ethylbenzene dehydrogenation decreases as the reaction temperature decreases. The decrease of temperature adversely affects not only the conversion level, but also the selectivity for styrene, since at equilibrium conditions, only undesirable side reactions continue to take place. Therefore, it is necessary to maintain the desired temperature level in order to provide a high equilibrium conversion level and a high reaction rate. In the conventional process, the maintenance of temperature is attained by reheating the product stream with the addition of superheated steam between dehydrogenation catalyst beds using a multicatalyst bed reactor system. However, consumption of the additional superheated steam is considerably high and makes the dehydrogenation process costly. Accordingly, significant process economic improvements over the conventional ethylbenzene dehydrogenation processes can be achieved if the reaction temperature is somehow maintained while eliminating or reducing the additional superheated steam. One method of providing for the maintenance of the reaction temperature is to introduce oxygen into the reaction mixture by way of oxygen or an oxygen-containing gas such as air which will burn the hydrogen formed during the dehydrogenation reaction, this combustion resulting in an exothermic reaction which will provide the necessary amount of heat and, in addition, will shift the equilibrium toward production of styrene since the hydrogen formed in the dehydrogenation is consumed. Consequently, a higher conversion and higher styrene selectivity are achievable.

The combustion of hydrogen with the oxygen in the oxygen-containing gas requires the presence of an oxidation catalyst. There are some key requirements for the oxidation catalyst to be usable for such a purpose. The most important catalytic property required is good catalytic stability since the oxidation catalyst must survive under very severe reaction conditions, namely at about 600° to 650° C. in the presence of steam. Under such conditions, porous inorganic materials such as aluminas, silicas and zeolites cannot maintain their pore structures for a long period of time, resulting in the permanent damage of catalysts prepared using such materials as supports, e.g., platinum supported on a porous high surface area alumina, silica, or zeolite. Secondly, the oxidation catalyst must be very active to achieve complete conversion of oxygen to avoid poisoning of iron-based dehydrogenation catalysts which are sensitively oxidized with oxygen to lose their dehydrogenation activities. Thirdly, the oxidation catalyst must be selective for oxidation of hydrogen. Otherwise, ethylbenzene and styrene are consumed to lower the efficiency of styrene production.

Various U.S. patents have described types of oxidation catalysts which may be employed in this process. For example, U.S. Pat. No. 3,437,703 describes a catalytic dehydrogenation process which employs, as a dehydrogenation catalyst, a composition known in the trade as Shell-105 which consists of from 87% to 90% ferric oxide, 2% to 3% chromium oxide, and from 8% to 10% of potassium oxide. In addition, another dehydrogenation catalyst which is employed comprises a mixture of nickel, calcium, chromic oxide, graphite with a major portion of a phosphate radical. In addition to these dehydrogenation catalysts, the reaction also employs a catalyst for the oxidation step of the process comprising platinum or palladium in elemental form or as a soluble salt. Another U.S. patent, namely U.S. Pat. No. 3,380,931, also discloses an oxidation catalyst which may be used in the oxidative dehydrogenation of compounds such as ethylbenzene to form styrene comprising an oxide of bismuth and an oxide of a metal of Group VIB of the Periodic Table such as molybdenum oxide, tungsten oxide or chromium oxide. In addition, the patent also states that minor amounts of arsenic may also be present in the catalytic composite as well as other metals or metalloids such as lead, silver, tin, manganese, phosphorus, silicon, boron and sulfur.

U.S. Pat. No. 3,855,330 discloses a method for the production of styrene in which ethylbenzene is treated in the vapor state by passage over a dehydrogenation catalyst and an oxidation catalyst while introducing oxygen into the reaction medium. The dehydrogenation catalysts which are employed are those which have been set forth in various prior U.S. patents and which may be similar in nature to the dehydrogenation catalysts previously discussed. The types of oxidation catalysts which may be employed will include platinum or palladium catalysts which are composited on alumina or molecular screens of the zeolite type which have been charged with ferrous, heavy or noble metals. The patent lists the types of catalysts which are employed including copper or various zeolites, platinum on alumina, platinum on spinel, platinum and sodium on zeolites, platinum, sodium and potassium on zeolites, etc.

U.S. Pat. No. 3,670,044 discloses a method for dehydrogenating cycloalkane, arylalkane and alkanes in the presence of gaseous hydrogen or mixture of gaseous hydrogen and gaseous oxygen using a catalyst composition comprising a Group VIII metal or a mixture of a Group VIII metal and a Group IVA metal deposited on a support comprising a Group II aluminate spinel. It is noted that the patentee teaches that added hydrogen is used in connection with the oxygen, and that when only oxygen is used, the conversion and selectivity are generally low. The addition of hydrogen is believed to be a significant disadvantage in the dehydrogenation process inasmuch as the equilibrium conversion is lowered. This is in contradistinction to the process of the present invention wherein the dehydrogenation process, prior to the oxidation step, is not effected in the presence of any added hydrogen. As will hereinafter be shown in greater detail, the present process results in the selective oxidation of hydrogen with a concomitantly lower selectivity to carbon monoxide and carbon dioxide. In addition, the patentee teaches the use of one catalyst for both dehydrogenation and oxidation which is in contrast to the separate dehydrogenation and oxidation catalysts which are used in the present process.

In addition to the aforementioned U.S. patents, another patent, namely U.S. Pat. No. 4,435,607, also discloses a method for the dehydrogenation of dehydrogenatable hydrocarbons utilizing a two-step process which includes dehydrogenation followed by a selective oxidation process. The catalyst which is employed for the selective oxidation will comprise a noble metal of Group VIII, a metal of Group IVA and, if so desired, a metal of Group IA or IIA of the Periodic Table composited on a highly porous inorganic support. However, as will hereinafter be shown in greater detail, we have now discovered that by utilizing, as the support for the metallic portions of the catalyst, a metal oxide which has been treated in a certain manner prior to use thereof will provide a superior catalyst to those which have been used in prior processes.

BRIEF SUMMARY OF THE INVENTION

This invention relates to a process for the dehydrogenation of dehydrogenatable hydrocarbons. More specifically, the invention is concerned with a process for the dehydrogenation of a dehydrogenatable hydrocarbon in which the hydrocarbon which is to undergo treatment is subjected to a dehydrogenation step in the presence of a dehydrogenation catalyst. This dehydrogenation step is followed by a selective oxidation step in which the product mixture which results from the aforementioned dehydrogenation step is treated in the presence of certain catalytic compositions of matter which are hereinafter set forth in greater detail in such a manner whereby the hydrogen which is present and which has resulted from the dehydrogenation step is selectively oxidized with a concomitant minimum oxidation of the hydrocarbons. By utilizing the particular support for the selective oxidation catalyst, it is possible to obtain the desired dehydrogenated hydrocarbons in a relatively high yield as well as maintaining the stability and activity of the catalyst to a greater degree than has heretofore been experienced. By maintaining the aforementioned stability and activity, it is possible to obviate the necessity for relatively frequent changes of the catalyst or, in the alternative, regenerating the catalyst, thereby adding to the commercial attractiveness and economical feasibility of the dehydrogenation process.

It is therefore an object of this invention to provide a process for the dehydrogenation of dehydrogenatable hydrocarbons.

A further object of this invention is to provide a catalyst for the selective oxidation step of the process whereby hydrogen which is formed during the dehydrogenation process will be selectively oxidized to the substantial exclusion of the oxidation of the hydrocarbons.

In one aspect an embodiment of this invention resides in a process for the dehydrogenation of a dehydrogenatable hydrocarbon with separate and intermediate selective oxidation of hydrogen which comprises (a) contacting said hydrocarbon with a dehydrogenation catalyst comprising an alkaline metal-promoted iron compound in a first-reaction dehydrogenation zone in the presence of steam at dehydrogenation conditions to produce a first-reaction dehydrogenation zone effluent stream comprising a mixture of unconverted hydrocarbons, dehydrogenated hydrocarbons, hydrogen and steam; (b) removing said first-reaction dehydrogenation zone effluent from said first-reaction dehydrogenation zone; (c) passing said removed first-reaction dehydrogenation zone effluent of step (b) to a second-reaction oxidation zone, which is separate and discrete from said first-reaction dehydrogenation zone; (d) contacting said first-reaction dehydrogenation zone effluent in said second-reaction oxidation zone with an oxygen-containing gas to selectively oxidize said hydrogen within said first-reaction zone effluent to the substantial exclusion of oxidation of said unconverted and dehydrogenated hydrocarbons in the presence of an oxidation catalyst consisting essentially of a Group VIII noble metal, a Group IVA metal and a Group IA or IIA metal composited on an alumina support at oxidation conditions wherein said exothermic selective oxidation of said hydrogen provides additional heat and thereby raises the temperature of said unconverted and dehydrogenated hydrocarbons; (e) withdrawing said unconverted and dehydrogenated hydrocarbons from said second-reaction oxidation zone having an increased temperature with respect to the temperature of said first-reaction dehydrogenation zone effluent; (f) passing said removed second-reaction oxidation zone product stream of step (e) to a third-reaction dehydrogenation zone containing a dehydrogenation catalyst comprising an alkaline metal-promoted iron compound at dehydrogenation conditions to produce dehydrogenated hydrocarbons; and (g) withdrawing and recovering said dehydrogenated hydrocarbons, the improvement which comprises calcining said alumina support of said oxidation catalyst used in step (d) at a temperature in the range of from about 900° to about 1500° C. prior to impregnation thereon of all of the metallic portions of said oxidation catalyst.

A specific embodiment of this invention is found in a process for the dehydrogenation of ethylbenzene which comprises contacting said ethylbenzene with a dehydrogenation catalyst comprising an alkaline metal modified iron catalyst at a temperature in the range of from about 500° to about 700° C. and a pressure in the range of from about 0.1 to about 10 atmospheres in the presence of steam, thereafter contacting the resultant mixture of unconverted ethylbenzene, styrene, hydrogen and steam with air at a temperature in the range of from about 500° to about 700° C. and a pressure in the range of from about 0.1 to about 10 atmospheres in the presence of a catalyst comprising a mixture of platinum, tin and lithium composited on an alumina support which has been calcined at a temperature in the range of from about 900° to about 1500° C. prior to impregnation thereon of the platinum, tin and lithium whereby hydrogen is selectively oxidized, and recovering the desired styrene.

Other objects and embodiments will be found in the following detailed description of the invention.

DETAILED DESCRIPTION OF THE INVENTION

As hereinbefore set forth, the present invention is concerned with a dehydrogenation process which involves the use, in one step of the process, of a selective oxidation catalyst which will provide increased stability as well as eliminating the shrinkage in the volume of the catalyst composition which is attendant with prior catalytic compositions of matter used in the same process.

In the present process, a dehydrogenatable hydrocarbon of the type hereinafter set forth in greater detail, is contacted with a dehydrogenation catalyst in the presence of steam in a multicatalyst bed system. Inasmuch as the dehydrogenation of the hydrocarbon is endothermic in nature, it is necessary to provide an additional amount of heat before the product enters the next catalyst bed, the reaction temperature being held at a relatively high rate in order to provide a high equilibrium conversion as well as a high reaction rate. One method of effecting this increase in the desired temperature is to provide an internal catalytic combustion of the hydrogen which is produced during the dehydrogenation reaction in order to reheat the product to the desired level. By effecting a selective oxidation of the hydrogen, it is possible to avoid the use of superheated steam or other outside sources of heat. This selective oxidation of hydrogen with the resultant composition thereof is effected by utilizing a selective oxidation catalyst of the type hereinafter set forth in greater detail, the selective oxidation catalyst maintaining its stability and activity for a considerable length of time.

The process of the present invention may be effected by utilizing an apparatus in which the dehydrogenation catalyst and the oxidative catalyst, both of the type hereinafter set forth in greater detail, are loaded in the apparatus in alternate layers. The number of alternate layers of dehydrogenation catalyst and selective oxidative catalyst may vary according to the size or type of apparatus which is employed, the number of alternate layers ranging from three to about nine. As will hereinafter be shown, the dehydrogenation catalyst and the oxidation catalyst are different in nature. Examples of dehydrogenation catalysts which may be employed will comprise an alkaline earth metal-promoted iron compound. The term "alkaline metal" as used in the present specification and appended claims will refer to metals of Groups IA and IIA of the Periodic Table which includes lithium, sodium, potassium, rubidium, cesium, beryllium, magnesium, calcium, strontium and barium. In addition, the promoted iron compound catalyst will, in the preferred embodiment of the invention, also include a compound containing a metal of Groups IVB, VB and VIB of the Periodic Table. For example, a typical dehydrogenation catalyst which may be employed in the process of this invention will consist essentially of about 85% by weight of ferric oxide, 12% by weight of potassium oxide, 2% by weight of chromia and 1% by weight of sodium hydroxide. Another typical dehydrogenation catalyst which may be used comprises 90% by weight of ferric oxide, 4% by weight of chromia and 6% by weight of potassium carbonate. In addition to these catalysts, other well-known dehydrogenation catalysts which may be utilized will include those comprising ferric oxide, potassium oxide, as well as other metal oxides and/or sulfides of metals of Groups IA, IIA, IVB, VB and VIB of the Periodic Table including those of calcium, lithium, strontium, magnesium, beryllium, zirconium, tungsten, molybdenum, hafnium, vanadium, copper, chromium and mixtures of two or more oxides such as chromia-alumina, chromia-titania, alumina-vanadia and the like.

The dehydrogenation of a dehydrogenatable hydrocarbon such as, for example, ethylbenzene, is effected by contacting the dehydrogenatable hydrocarbon and steam, in the absence of any added hydrogen, with the aforesaid catalyst at dehydrogenation conditions which are in the range of from about 500° to about 700° C. and at a reaction pressure in the range of from about 0.1 to about 10 atmospheres; the exact dehydrogenation conditions are, however, a function of the particular dehydrogenatable hydrocarbon undergoing dehydrogenation. Other reaction conditions will include a Liquid Hourly Space Velocity based on the hydrocarbon charge of from about 0.1 to about 10 hrs$^{-1}$ and steam to hydrocarbon weight ratios ranging from about 1:1 to about 40:1. The number of dehydrogenation zones of the catalyst beds may vary from 1 to about 5 in number and typically may comprise three reaction zones; however, the number of zones is not critical to the invention. After contacting the dehydrogenation catalyst with the steam and hydrocarbon, the resulting mixture comprising unconverted hydrocarbon, dehydrogenated hydrocarbon, steam and hydrogen which has passed through the catalyst bed is contacted in a separate zone with the selective oxidative catalytic composition of the type hereinafter set forth in greater detail. In addition, oxygen-containing gas is introduced into the reactor, preferably at a point adjacent to the oxidative catalyst bed. Examples of oxygen-containing bases which may be utilized to effect the selective oxidation of the hydrogen which is present will include air, oxygen, air or oxygen diluted with other gases such as steam, carbon dioxide and inert gases such as nitrogen, argon, helium, etc. The amount of oxygen which is introduced to contact the product stream may range from about 0.1:1 to about 2:1 moles of oxygen per mole of hydrogen contained in the product stream. In this particular reaction zone, the product stream, which comprises unreacted dehydrogenatable hydrocarbon, dehydrogenated hydrocarbon, hydrogen and steam, undergoes a selective oxidation in contact with oxygen and the oxidative catalyst whereby hydrogen is selectively oxidized to water with a minimal amount of reaction of oxygen with the hydrocarbons, either unconverted hydrocarbon or dehydrogenated hydrocarbon.

After passage through the zone containing the oxidation catalyst, the mixture may then be passed through a second dehydrogenation zone containing a dehydrogenation catalyst of the type hereinbefore set forth for further dehydrogenation, the process being completed through the plurality of zones followed by withdrawal of the product stream and separation of the unconverted hydrocarbon from the desired dehydrogenated product.

It is contemplated that the dehydrogenation process for the dehydrogenation of dehydrogenatable hydrocarbons utilizing the oxidative catalytic compositions of matter of the present invention will be applicable to a wide variety of dehydrogenatable hydrocarbons. Examples of hydrocarbons which are susceptible to a dehydrogenation process utilizing the catalysts of the present invention will include lower alkyl-substituted aromatic hydrocarbons such as ethylbenzene, diethylbenzene, isopropylbenzene, diisopropylbenzene, o-ethyltoluene, m-ethyltoluene, p-ethyltoluene, o-isopropyltoluene, m-isopropyltoluene, p-isopropyltoluene, ethylnaphthalene, propylnaphthalene, isopropylnaphthalene, diethylnaphthalene, etc., paraffins such as ethane, propane, n-butane, isobutane, n-pentane, isopentane, n-hexane, n-heptane, n-octane, n-nonane, n-decane, and branched chain isomers thereof, cycloparaffins such as cyclobutane, cyclopentane, cyclohexane, methylcyclopentane, methylcyclohexane, ethylcyclopentane, olefins such as 1-butene, 2-butene, 1-pentene, 2-pentene, 1-hexene, 2-hexene, 3-hexene, and branched chain derivatives thereof, etc.

The selective oxidation step of the process utilizes, as hereinbefore set forth, the hydrogen which has been produced in the dehydrogenation step of the process to supply heat to the inlet of the next dehydrogenation catalyst bed. Inasmuch as temperatures which are utilized in the process may be as high as 650° C. in the presence of steam, the operating conditions in which the oxidation catalyst must function are severe in nature. In order for the oxidation catalyst to remain stable and minimize the carbon formation thereon, the catalyst support must be calcined at a relatively high temperature in order to decrease the surface area, this decrease in surface area contributing to the stability of the catalyst. Conventional oxidation catalysts utilizing a porous support such as alumina which had been calcined at relatively low temperatures, i.e., below about 900° C. or lower, lose surface area at a rapid rate and form excessive carbon on the surface thereof, thus resulting in a deactivation of the catalyst.

A relatively effective oxidation catalyst which may be used in the dehydrogenation and selective oxidation process comprises a noble metal of Group VIII of the Periodic Table such as platinum composited on alpha-alumina. However, the production of alpha-alumina is accomplished by calcining a relatively high surface area alumina such as gamma-alumina at temperatures of about 1650° C. The calcination of gamma-alumina at this temperature, while resulting in the formation of alpha-alumina, has a deleterious effect in that the loss in volume yield or shrinkage may be from about 35% to 60% or more of the original volume. In addition, the use of such a high calcination temperature also contributes to the cost of the catalyst by utilization of a relatively high amount of energy, thus making the catalyst more expensive in nature. Therefore, it is incumbent to obtain a catalyst support upon which the catalytic metal or metals portion of the finished catalyst composite may be impregnated. It has now been discovered that by subjecting the porous support as an alumina to a calcination temperature within the range of 900° C. to about 1500° C. prior to impregnation thereon of the metals thereon, provides a catalyst which possesses greater stability in terms of activity and length of service than is possessed by other selective oxidation catalyts which do not utilize this type of support. The calcination of the support at the aforementioned temperatures will result in the obtention of a catalyst which may be prepared at a decreased cost in manufacturing and with a concomitant improved yield of the finished catalyst composite. The aforementioned calcination of the porous support portion of the finished composite may be effected in a dry or nonhydrous atmosphere, preferably in a range of from about 1100° to about 1500° C. or, if so desired, the calcination may be effected in a hydrous or steam atmosphere at temperatures preferably in the range of from about 900° to about 1200° C. The calcination of the supports within this temperature range will convert the alumina into a more refractory and chemically inert form which possesses a relatively low surface area which is less than about 80 m$^2$/g and preferably which may range from about 1 to about 40 m$^2$/g. The calcination of the support within the temperature range hereinbefore set forth will be effected over a period of time which may range from about 0.5 to about 30 hours or more in duration. It is to be understood that the particular temperature which is selected for the calcination step will influence or direct the time frame during which the calcination takes place, for example, when effecting the calcination within the lower portion of either of the two ranges set forth, a longer period of time will be employed while reversibly, if the calcination is effected within the higher portion of the ranges, a shorter period of time may be employed. When effecting the calcination in a hydrous or steam atmosphere, it is contemplated that the steam content of the atmosphere may range from a relatively low 2% up to about 100%.

The alumina support which has been calcined within the range of temperatures previously discussed will possess certain characteristics or properties which enhance the stability of the catalyst after impregnation of the desired metals thereon. The final porous support will possess a piece density in the range of from about 0.3 to about 2.5 g/cc; a pore volume less than about 0.5 cc/g; a surface area in a range of from about 1 to about 80 m$^2$/g, an ABD of from about 0.3 to about 1.1 and for the alumina phase alpha-alumina or a mixture of alpha alumina and theta alumina.

The selective oxidation catalysts which are employed in the process of this invention will comprise a noble metal of Group VIII of the Periodic Table and a metal of Group IVA of the Periodic Table composited on a solid inorganic support which, prior to the compositing of the metals thereon, has been calcined at a temperature within the range herebefore discussed. In addition, if so desired, it is also contemplated within the scope of this invention that the catalyst composite will also contain a metal selected from Groups IA and IIA of the Periodic Table. Of the noble metals of Group VIII of the Periodic Table, platinum, palladium and rhodium comprise the preferred species, said metals being present in the final composite in an amount in the range of from about 0.01% to about 5% by weight. Of the metals of Group IVA of the Periodic Table, germanium, tin and lead comprise the preferred species, these metals also being present in the final catalyst composite in an amount in the range of from about 0.01% to about 5% by weight. It is also contemplated within the scope of this invention that metals of Groups IIIB and IIIA such as scandium, yttrium, lanthanum, boron, gallium, indium and thallium may also be employed in a range of from about 0.1 to about 20% by weight in place or in conjunction with the metal of Group IVA if so desired. The preferred species of metals of Group IA or IIA of the Periodic Table will include potassium, sodium, lithium, rubidium, cesium, barium, francium, and radium, the alkali metals or alkaline earth metals being present in an amount in the range of from about 0.01% to about 10% by weight of the catalyst composite.

The aforesaid metals are composited on a solid inorganic support which possesses a necessary highly porous configuration; some specific examples of these supports which may be employed will include theta-alumina, silica, mixtures of inorganic oxides such as silica-alumina, silica-zirconia, alumina-zirconia-silica, silicon carbide, etc. The selective oxidation catalyst which is utilized in the process of this invention may be prepared in any suitable manner known in the art. For example, one type of preparation will comprise impregnating the solid support which may be in the form of beads, spheres, pellets, etc. with an aqueous solution of a Group VIII metal compound of the Periodic Table. The aqueous solution of the noble metal-containing compound may be prepared from soluble salts of these metals, such as chloroplatinic acid, chloropalladic acid, rhodium chloride, platinum sulfate, palladium sulfate, etc. The solid support is impregnated with the solution for a period of time which is sufficient to allow the deposition of the desired amount of the noble metal on the solid support, that is, an amount sufficient so that the finished catalytic composition will contain from about 0.01% to about 5% by weight of the composite. After recovery of the impregnated solid support, the composite is then dried and calcined at a temperature in the range of from about 500° to about 600° C. or more in an air atmosphere in the absence or presence of steam.

The thus formed composite containing a noble metal may then be further impregnated with an aqueous solution of a metal of Group IVA of the Periodic Table. In a similar manner to that hereinbefore described, the amount of soluble salts such as tin chloride, tin bromide, tin sulfate, lead chloride, lead persulfate, germanium chloride, etc. will be present in the solution sufficient so that the finished catalytic composition will contain the desired amount of metals. Again, the impregnation is allowed to proceed for a predetermined period of time following which the composite is recovered, dried and calcined. In the event that it is desired to have a metal of Group IV or IIA of the Periodic Table present in the catalyst composite, the third step of the process is effected in a similar manner by subjecting the composite to an impregnation utilizing an aqueous solution containing the desired metal. Examples of salts of these metals which may be employed will include potassium chloride, potassium bromide, potassium iodide, potassium nitrate, potassium sulfate, potassium acetate, potassium propionate, rubidium chloride, rubidium bromide, rubidium iodide, rubidium nitrate, rubidium sulfate, rubidium acetate, rubidium propionate, cesium chloride, cesium bromide, cesium iodide, cesium nitrate, cesium sulfate, cesium acetate, cesium propionate, calcium chloride, barium chloride, barium bromide, barium iodide, barium nitrate, barium sulfate, barium acetate, barium propionate, etc. After allowing the impregnation to proceed for a period of time sufficient to permit the deposition of the desired amount of metal on the catalyst, the composite is recovered, dried and calcined at a temperature within the range hereinbefore set forth, and recovered.

The incorporation of Group IVA metal may also be carried out in the support forming step. Addition of tin, for example, may be added in the preparation of the alumina support whether it be by oil-dropping of spheres or extrusion of an alumina dough. The tin incorporation may also be a combination of tin in sol and impregnated tin.

It is also contemplated that the preparation of the selective oxidation catalyst may be prepared by coimpregnating the noble metal of Group VIII of the Periodic Table, the metal of Group IVA of the Periodic Table, and, if so desired, the metal of Group IA or IIA of the Periodic Table on the solid support. When such a type of preparation is employed, the solid support, such as alumina, is impregnated with an aqueous or acidic solution containing salts of the noble metal and the Group IVA metal along with, if so desired, the alkali metal or alkaline earth metal in a manner similar to that hereinbefore set forth. After allowing the impregnation to proceed for a predetermined period of time, the composite is recovered, dried and calcined at a temperature within the range hereinbefore set forth in an air atmosphere in the absence or presence of steam, following which it is recovered for use in the oxidation portion of the process of the present invention.

Some specific examples of selective oxidation catalytic compositions of matter which may be used in the process of the present invention will include platinum, germanium and potassium composited on alumina, palladium, germanium and potassium composited on alumina, rhodium, germanium and potassium composited on alumina, platinum, tin and potassium composited on alumina, palladium, tin and potassium composited on alumina, rhodium, tin and potassium composited on alumina, platinum, germanium and cesium composited on alumina, palladium, germanium and cesium composited on alumina, rhodium, germanium and cesium composited on alumina, platinum, tin and cesium composited on alumina, palladium, tin and cesium composited on alumina, rhodium, tin and cesium composited on alumina, platinum, germanium and barium composited on alumina, palladium, germanium and barium composited on alumina, rhodium, germanium and barium composited on alumina, platinum, tin and barium composited on alumina, palladium, tin and barium composited on alumina, rhodium, tin and barium composited on alumina, platinum, lead and potassium composited on alumina, palladium, lead and potassium composited on alumina, rhodium, lead and potassium composited on alumina, platinum, lithium and indium composited on alumina, platinum, lithium and lanthanum composited on alumina, palladium, potassium and indium composited on alumina, etc. It is to be understood that the above enumerated catalysts are only representative of the selective oxidation composites which may be used in the process of this invention, and that said invention is not necessarily limited thereto. By utilizing a selective oxidative catalytic composition of matter in a process which involves the dehydrogenation of dehydrogenatable hydrocarbons, it is possible to obtain a process which, in addition to obtaining a desirable and commercially attractive yield of dehydrogenation products, also permits the operation of the process in an economically viable manner due to the catalytic stability of the catalyst under the relatively harsh and stringent operating conditions such as high temperature and high concentration of steam at which the process is operated. This is in contradistinction to prior art types of oxidative catalysts which do not possess the stability of the present catalysts and cannot survive for a long period of time, thus making the commercial use of such catalysts unattractive due to the necessity of having to replace or regenerate the catalyst after a short interval of operating time has elapsed. In addition, the catalysts of the present invention also exhibit a definite affinity for the selective oxidation of hydrogen rather than a tendency for the oxidation of the dehydrogenated products.

The following examples are given for purposes of illustrating the process of the present invention utilizing a selective oxidation catalyst in said process. However, it is to be understood that these examples are given merely for purposes of illustration and that the present invention is not necessarily limited thereto.

EXAMPLE I

A selective oxidation catalyst was prepared by adding 44.1 grams of concentrated nitric acid to 623.6 grams of water followed by the addition of 7.6 grams of tin chloride. The resulting solution was then added to 1139.6 grams of alumina, the solution was mixed slowly for 15 seconds followed by a more vigorous mixing for a period of five minutes. The resulting dough material was then extruded through a die which possessed 4.2 mm diameter holes using a double auger extruder. The extrudate was then dried in an oven for a period of two hours at a temperature of 95° C. The procedure was repeated to yield a total of 3043 grams of oven dried extrudate. A first calcination of the extrudate was accomplished by placing 2943 grams of the oven dried extrudates in a quartz tube and calcined by subjecting the extrudates to a temperature increase from room temperature to 350° C. in an air atmosphere passing over the catalyst at a rate of about 0.5 liters per minute during a period of 1.5 hours. Upon reaching the 350° C. temperature point, the extrudate was dried at this temperature in an air atmosphere for an additional period of one hour. Thereafter, the temperature was increased to 600° C. while maintaining an air flow of 0.5 liters per minute and after reaching 600° C. was maintained at this temperature for a period of three hours at the same air flow previously described. At the end of the three hour period, the extrudate was allowed to cool to room temperature and recovered.

Approximately 535.0 grams (740 cc) of the precalcined extrudate was loaded onto a ceramic tray and heated to a temperature of 1040° C. over a period of six hours. Upon reaching this temperature, the material was maintained thereat for an additional period of three hours and thereafter slowly cooled to room temperature over another period of six hours.

The finished oxidation catalyst was then prepared by adding 12.91 grams of a chloroplatinic acid solution containing 2.54% by weight of platinum, 37.27 grams of lithium nitrate solution containing 0.88% by weight of lithium and 7.3 grams of concentrated nitric acid to 142.5 grams of water. The solution was mixed and added to a glass steam-jacketed evaporator. Thereafter, 163.57 grams (200 cc) of the calcined extrudate was added to the evaporator, the evaporator was rotated for 15 minutes at room temperature and steam was introduced into the steam jacket. The evaporator was rotated for two hours with a stream of nitrogen at a rate of about 1 liter per minute purging at the mouth of the evaporator. Following this, the introduction of steam was discontinued, the impregnated extrudates were removed, dried in an oven for a period of two hours at a temperature of 150° C. and thereafter calcined in a quartz tube. The calcination of the impregnated extrudate was accomplished by heating the quartz tube from room temperature to 650° C. in a flowing atmosphere of air in which the air passed through the tube at a rate of about 0.5 liters per minute for a period of two hours. Upon reaching 650° C., the temperature was maintained thereat for a period of two hours while subjecting the extrudate to a flow of air at a rate of 0.5 liters per minute, said air stream having been bubbled through a $H_2O$ bubbler which was heated to a temperature of 65° C. At the end of the two hour period, the $H_2O$ bubbler was bypassed and air was passed over the catalyst for an additional period of one hour, the temperature of the tube being still maintained at 650° C. At the end of the additional one hour, heating was discontinued, the extrudate was cooled to room temperature in a stream of air again at a rate of 0.5 liters per minute and recovered.

Two additional selective oxidation catalysts were prepared in a manner similar to that set forth in the above paragraphs, the differences in the catalyst preparation being in the high temperature calcination step of the process. Catalyst A which was prepared according to the above paragraph and which was calcined at 1040° C. was labeled "A"; the catalyst which was calcined at a temperature of 1140° C. was labeled "B" and the catalyst which was calcined at 1230° C. was labeled "C."

The properties of the three catalysts, A, B, and C, are set forth in Table 1 below:

TABLE 1

| Catalyst | Surface Area $m^2/g$ | Piece Density g/cc | wt. % Pt | wt. % Sn | wt. % Li |
|---|---|---|---|---|---|
| A | 106 | 1.51 | 0.200 | 0.50 | 0.20 |
| B | 17 | 2.18 | 0.180 | 0.47 | 0.19 |
| C | 4 | 2.43 | 0.168 | 0.53 | 0.20 |

EXAMPLE II

The three catalysts which were prepared according to the above example were utilized in a selective oxidation test and were evaluated for oxygen conversion and selectivity for oxygen reacting with hydrogen to form water. The catalysts in an amount of 50 cc were loaded into a $\frac{7}{8}''$ inner diameter stainless steel reactor having a 10" long $\frac{1}{2}''$ diameter bore for the catalyst loading. The reactor was heated to an inlet temperature of 570° C. and a feedstream comprising a mixture of ethylbenzene, styrene, steam, hydrogen, oxygen and nitrogen which simulated a product stream at about a 60% ethylbenzene conversion from the second dehydrogenation catalyst bed of a three dehydrogenation catalyst bed reactor system having an oxidation catalyst bed positioned between the dehydrogenation catalyst beds was fed to the reactor. The feedstream was passed over the oxidation catalyst bed at the aforesaid inlet temperature and at a reactor outlet pressure of 0.7 atmospheres. The hydrogen feed was maintained at a Liquid Hourly Space Velocity of 10.3 hours$^{-1}$. The inlet feed ratio of the feedstream of ethylbenzene and styrene/$H_2O$/$H_2$/$O_2$/$N_2$ was 1.0/9/0.45/0.13/1. In addition, the air into the catalyst bed was controlled in order to maintain a maximum temperature of 630° C. in the reactor up to a specified limit of added air. The conversion of oxygen was plotted for a period of 100 hours, the results of said run being set forth in Table 2 below. In this table, column D is the % of oxygen converted and column E is the styrene combustion selectivity as set forth in mole percent.

TABLE 2

| Hrs. on Stream | Catalyst A D | Catalyst A E | Catalyst B D | Catalyst B E | Catalyst C D | Catalyst C E |
|---|---|---|---|---|---|---|
| 20 | 92 | 6.8 | 100 | 8.0 | 94 | 11.0 |
| 40 | 82 | 7.5 | 98 | 7.5 | 99 | 9.9 |
| 80 | 70 | 7.3 | 96 | 7.3 | 98 | 10.2 |
| 100 | — | — | 96 | 7.3 | 96 | 9.8 |

The maximum catalyst bed temperature as a function of time on stream is shown in Table 3 for catalysts A, B, and C.

TABLE 3

Maximum Temperature of Catalyst Bed

| Hrs. on Stream | Catalyst A | Catalyst B | Catalyst C |
|---|---|---|---|
| 20 | 612° C. | 629° C. | 630° C. |
| 40 | 612° C. | 628° C. | 630° C. |
| 80 | 602° C. | 622° C. | 630° C. |
| 100 | — | 622° C. | 630° C. |

It is to be noted from the above tables that the catalysts which were prepared from the alumina support having been calcined at temperatures greater than 1100° C. in the absence of steam possessed significantly higher catalytic stability than did the other catalysts.

EXAMPLE III

As a further illustration of the stability of selective oxidation catalysts in which the support has been calcined within a range hereinbefore set forth in greater detail, two oxidation catalysts were prepared. The first catalyst was prepared by calcining an alumina support at a temperature of 1649° C. The resulting alumina which possessed an ABD of 1.40 g/cc, was impregnated with a chloroplatinic acid solution, dried and calcined, and the catalyst which contained 0.2% by weight of platinum was tested in a standard accelerated oxidation test. The test was effected in a manner similar to that set forth in Example II above utilizing an ethylbenzene/styrene/$H_2O$/$H_2$/$O_2$/$N_2$ molar feed ratio of 1/1.48/17.9/1.14/0.25/2.21 feed stream. The reaction conditions included an inlet temperature of 600° C., a pressure of 0.5 atmospheres at the reactor outlet and a Liquid Hourly Space Velocity of $100^{-1}$ based upon the ethylbenzene/styrene. The initial oxygen conversion was 84% and decreased to 46% over a period of 144 hours. In addition, the selectivity of oxygen reacting with hydrocarbons to $CO_2$+CO ranged from about 11% to about 14%.

In contrast to this, a second catalyst was prepared by calcining alumina at a temperature of 1200° C. to prepare a support which possessed an ABD of 0.94. The support was impregnated with chloroplatinic acid and treated so that the final composite again contained 0.2% by weight of platinum. The catalyst was used in a standard accelerated oxidation test using conditions similar to that set forth in the above paragraph. The results which were obtained when using the catalyst of the present invention included an oxygen conversion which decreased from an initial conversion of 82% down only to 60% at the end of 144 hours. In addition, the selectivity for oxygen reacted with hydrocarbons to $CO_2$+CO was significantly lower, ranging from about 5% to about 8%.

It is therefore readily apparent from the above comparisons that the catalysts in which the porous supports have been calcined at a temperature within the ranges hereinbefore set forth will exhibit a greater stability with regard to oxygen conversion as well as selectivity to hydrogen than do the catalysts in which the porous support has been calcined at a relatively high temperature.

EXAMPLE IV

A selective oxidation catalyst was prepared by adding 134.2 grams of lanthanum nitrate to 458.4 grams of water. In addition, 15.0 grams of nitric acid and 7.3 grams of tin chloride were also added. The resulting solution was then added to 547 grams of alumina and the solution was mixed for a period of five minutes. The resulting doughy material was then extruded through a die which possessed 4.2 mm diameter holes using a double auger extruder.

The extrudate was then dried in an oven for a period of two hours at a temperature of 95° C. to yield 484.2 grams of oven-dried extrudate. A first calcination of the extrudate was effected by placing 327 grams (500 cc) of the oven dried-extrudates in a quartz tube. The extrudates were calcined by subjecting them to a temperature increase from room temperature to 350° C. in an air atmosphere which passed over the catalyst at a rate of about 1.5 liters per minute during a period of 0.5 hours. Upon reaching 350° C. the extrudate was dried at this temperature in an air atmosphere for an additional period of one hour. Thereafter, the temperature was increased to 600° C. and maintained thereat for a period of three hours in the presence of an air flow of 0.5 liters per minute. At the end of this time, heating was discontinued and the extrudate was allowed to cool to room temperature.

The high temperature calcination of the base was accomplished by loading 197.36 grams (425 cc) of the precalcined extrudate onto a ceramic tray which was then heated to a temperature of 1330° C. during a period of eight hours. Upon reaching this temperature the extrudate was calcined thereat for a period of three hours and thereafter slowly cooled to room temperature over an additional period of eight hours to yield 195.3 grams (350 cc) of the base.

The finished oxidation catalyst was then prepared by adding 11.31 grams of chloroplatinic acid (2.49% Pt), 13.78 grams of lithium nitrate (1.02% Li), 3.14 grams of nitric acid and 97 grams of water to 69.74 grams (125 cc) of the calcined extrudate, said addition being effected in a glass steam-jacketed evaporator. The evaporator was rotated for 15 minutes at room temperature and steam was introduced into the jacket. The evaporator was rotated for a period of two hours with a stream of nitrogen at a rate of one liter per minute purging at the mouth of the evaporator. Following this, the introduction of steam was discontinued, and the impregnated extrudates were recovered and dried in an oven for a period of two hours at a temperature of 150° C.

The impregnated extrudate was calcined by heating a quartz tube containing the extrudate to a temperature of 650° C. in a flowing rate of air, the air being passed over the extrudate at a rate of 0.5 liters per minute for a period of two hours. Upon reaching 650° C. the temperature was maintained thereat for an additional period of two hours while passing a stream of air which had been bubbled through an $H_2O$ bubbler heated to 65° C. at a rate of 0.5 liters per minute over the extrudate. At the end of two hours, the bubbler was bypassed and air was passed over the extrudate for one hour at 650° C. At the end of this period, the heating was discontinued and the extrudate was cooled to room temperature in a flow of air.

The cooled catalyst which was recovered contained 0.4 wt. % platinum, 0.2 wt. % lithium, 1.0 wt. % tin, and 12.5 wt. % lanthanum, said catalyst having a surface area of 9 m$^2$/g.

EXAMPLE V

Yet another selective oxidation catalyst may be prepared in a manner similar to that set forth in the above examples, the alumina base being prepared by admixing nitric acid, water and alumina. The resulting material may be extruded through a die and the extrudate calcined under conditions similar to that previously described. The first calcination of the extrudate may be accomplished at a temperature of 650° C. and the final high temperature impregnation may be effected at a temperature of 1300° C., the first calcination and final calcination being effected over a period of time similar to those previously set forth.

The finished oxidation catalyst may then be prepared by adding solutions of chloroplatinic acid, lithium nitrate, nitric acid and indium chloride to the calcined extrudate which may then be further calcined by utilizing a procedure similar to that set forth in Example I above. Following the final calcination, the resultant catalyst system may be recovered and utilized in a selective oxidation procedure whereby, in a dehydrogenation reaction, hydrogen is selectively oxidized in preference to the hydrocarbons present in the reaction mixture.

We claim as our invention:

1. In a process for the dehydrogenation of dehydrogenatable hydrocarbon with separate and intermediate selective oxidation of hydrogen which comprises:
   (a) contacting said hydrocarbon with a dehydrogenation catalyst comprising an alkaline metal-promoted iron compound in a first-reaction dehydrogenation zone in the presence of steam at dehydrogenation conditions to produce a first-reaction dehydrogenation zone effluent stream comprising a mixture of unconverted hydrocarbons, dehydrogenated hydrocarbons, hydrogen and steam;
   (b) removing said first-reaction dehydrogenation zone effluent from said first-reaction dehydrogenation zone;
   (c) passing said removed first-reaction dehydrogenation zone effluent of step (b) to a second-reaction oxidation zone, which is separate and discrete from said first-reaction dehydrogenation zone;
   (d) contacting said first-reaction dehydrogenation zone effluent in said second-reaction oxidation zone with an oxygen-containing gas to selectively oxidize said hydrogen within said first-reaction zone effluent to the substantial exclusion of oxidation of said unconverted and dehydrogenated hydrocarbons in the presence of an oxidation catalyst consisting essentially of a Group VIII noble metal, a Group IVA metal, and a Group IA or IIA metal composited on an alumina support at oxidation conditions wherein said exothermic selective oxidation of said hydrogen provides additional heat and thereby raises the temperature of said unconverted and dehydrogenated hydrocarbons;
   (e) withdrawing said unconverted and dehydrogenated hydrocarbons from said second-reaction oxidation zone having an increased temperature with respect to the temperature of said first-reaction dehydrogenation zone effluent;
   (f) passing said removed second-reaction oxidation zone product stream of step (e) to a third-reaction dehydrogenation zone containing a dehydrogenation catalyst comprising an alkaline metal-promoted iron compound at dehydrogenation conditions to produce dehydrogenated hydrocarbons; and
   (g) withdrawing and recovering said dehydrogenated hydrocarbons, the improvement which comprises calcining said alumina support of said oxidation catalyst used in step (d) at a temperature in the range of from about 900° to about 1500° C. prior to impregnation thereon of all of the metallic portions of said oxidation catalyst.

2. The process of claim 1 further characterized in that said calcination of said alumina support is effected in the presence of steam.

3. The process of claim 1 in which said dehydrogenation and oxidation conditions include a temperature in the range of from about 500° to about 700° C. and a pressure in the range of from about 0.1 to about 10 atmospheres.

4. The process of claim 1 in which said Group VIII noble metal is present in said oxidation catalyst in an amount in the range of from about 0.01% to about 5% by weight of said catalyst.

5. The process of claim 1 in which said Group IVA metal is present in said oxidation catalyst in an amount in the range of from about 0.01% to about 5% by weight of said catalyst.

6. The process of claim 1 in which said Group IA or IIA metal is present in said oxidation catalyst in an amount in the range of from about 0.01% to about 10% by weight of said catalyst.

7. The process of claim 1 in which said alkaline metal of said dehydrogenation catalyst is selected from the group consisting of Group IA and IIA of the Periodic Table.

8. The process of claim 1 in which said dehydrogenation catalyst contains an oxide or a sulfide of a metal selected from the group consisting of Groups IVB, VB and VIB of the Periodic Table.

9. The process of claim 1 in which said Group VIII noble metal of the Periodic Table is selected from the group consisting of platinum, palladium and rhodium.

10. The process of claim 1 in which the metal of Group IVA of the Periodic Table is selected from the group consisting of germanium, lead, and tin.

11. The process of claim 1 in which the metal of Group IA or IIA of the Periodic Table in the oxidation catalyst is selected from the group consisting of lithium, sodium, potassium, rubidium, cesium, beryllium, magnesium, calcium, strontium and barium.

12. The process as set forth in claim 1 further characterized in that said oxidation catalyst contains a metal of Group IIIA or IIIB of the Periodic Table selected from the group consisting of scandium, yttrium, lanthanum, boron, gallium, indium and thallium.

13. The process of claim 1 in which said oxygen-containing gas is air.

14. The process of claim 1 in which said oxygen-containing gas is oxygen.

15. The process of claim 1 in which said dehydrogenatable hydrocarbon is ethylbenzene and said dehydrogenated hydrocarbon is styrene.

16. A process for the dehydrogenation of dehydrogenatable hydrocarbons with separate and intermediate selective oxidation of hydrogen which comprises contacting a dehydrogenation zone effluent comprising a mixture of unconverted hydrocarbons, dehydrogenated hydrocarbons, hydrogen and steam with an oxygen-containing gas in the presence of an oxidation catalyst consisting essentially of a Group VIII noble metal, a Group IVA metal and a Group IA or IIA metal composited on an alumina support which has been calcined at a temperature in the range of from about 900° to about 1500° C. prior to impregnation thereon of all of the metallic portions of said oxidation catalyst at oxidation conditions to selectively oxidize said hydrogen in said effluent to the substantial exclusion of oxidation of said unconverted and dehydrogenated hydrocarbons, withdrawing and recovering said hydrogenated hydrocarbons.

17. The process as set forth in claim 16 in which said calcination of said alumina is effected in the presence of steam.

18. The process as set forth in claim 16 in which said oxidation conditions include a temperature in the range of from about 500° to about 700° C. and a pressure in the range of from about 0.1 to about 10 atmospheres.

19. The process as set forth in claim 16 in which said Group VIII noble metal is present in said oxidation catalyst in an amount in the range of from about 0.01% to about 5% by weight of said catalyst, said Group IVA metal is present in an amount in the range of from about 0.01% to about 5% by weight of said oxidation catalyst and said Group IA or IIA metal is present in an amount in the range of from about 0.01% to about 10% by weight of said catalyst.

20. The process as set forth in claim 16 in which said unconverted hydrocarbon is ethylbenzene and said dehydrogenated hydrocarbon is styrene.

* * * * *

UNITED STATES PATENT AND TRADEMARK OFFICE
CERTIFICATE OF CORRECTION

PATENT NO. : 4,565,898
DATED : January 21, 1986
INVENTOR(S) : O'Hara et al.

It is certified that error appears in the above-identified patent and that said Letters Patent is hereby corrected as shown below:

Column 17, line 19, change "hydrogenated" to --dehydrogenated--.

Signed and Sealed this

Tenth Day of June 1986

[SEAL]

Attest:

DONALD J. QUIGG

Attesting Officer

Commissioner of Patents and Trademarks